United States Patent [19]
Lin et al.

[11] Patent Number: 5,615,276
[45] Date of Patent: Mar. 25, 1997

[54] METHOD OF MEASURING LOW INTERFACIAL TENSION BY PENDANT DROP DIGITIZATION

[75] Inventors: Shi-Yow Lin, Taipei; Hae-Feng Hwang, Hsinchu, both of Taiwan

[73] Assignee: National Science Council, Taipei, Taiwan

[21] Appl. No.: 502,498

[22] Filed: Jul. 14, 1995

[51] Int. Cl.$^6$ ................................................ G06K 9/00
[52] U.S. Cl. .......................... 382/100; 73/64.48; 73/64.52
[58] Field of Search .......................... 382/100; 73/64.68, 73/64.52; 324/71.4

[56] References Cited

PUBLICATIONS

Shi-Yow Lin, et al., "Diffusion-Limited Interpretation of the Induction Period in the Relaxation in Surface Tension Due to the Adsorption of Straight Chain, Small Polar Group Surfactant: Theory and Experiment," Langmuir 1991, 7, 1055–1066.

Shi-Yow Lin, et al., "Diffusion–Controlled Surfactant Adsorption Studied by Pendant Drop Digitization," AIChe J., Dec. 1990, vol. 36, No. 12, 1785–1795.

Shi-Yow Lin, et al., "Measurement of Low Interfacial Tension by Pendant Drop Digitization," Langmuir 1994, 10, 4703–4709.

*Primary Examiner*—Jose L. Couso
*Assistant Examiner*—Anh Hong Do
*Attorney, Agent, or Firm*—Hitt Chwang & Gaines, P.C.

[57] ABSTRACT

The present invention is related to a method of measuring low interfacial tension of a two-phase fluid system by pendant drop digitization, in which a silhouette of a pendant drop is created and photographed, its video image is digitized, and a plurality of the digitized data points are then repeatedly compared with theoretical curves calculated numerically from Young Laplace equation to obtain the interfacial tension.

1 Claim, 13 Drawing Sheets

METHOD OF MEASURING LOW INTERFACIAL TENSION BY PENDANT DROP DIGITIZATION

FIELD OF THE INVENTION

The present invention is related to a method of measuring low interfacial tension of a two-phase fluid system, in particular to a method comprising digitizing a video image of a silhouette of a pendant drop, and repeatedly comparing a plurality of the digitized data points with theoretical curves calculated numerically from Young Laplace equation to obtain the interfacial tension.

BACKGROUND OF THE INVENTION

The measurement of ultralow interfacial tension is of intrinsic interest in oil-water systems. Interfacial tensions in such system are relevant to the understanding of various phenomena, e.g., the thermodynamics of formation of microemulsions and the mechanism of tertiary oil recovery such as micellar flooding and interfacial tension flooding. It is known that the tertiary oil recovery technique can enhance the oil recovery up to about 80% of all the oil reserve in the oil reservoir. The interfacial tension of an oil-water system is about 50 mN/m which is decreased to a level of $10^{-2}$ mN/m or even to a ultralow level of $10^{-4} \sim 10^{-5}$ mN/m after an appropriate surfactant being added to the oil-water system. There are various methods for measuring interfacial tension of a two-phase fluid system known in the art, for example capillary rise method, pendant drop method, spinning drop method, light scattering method, drop weight method, drop volume method, maximum bubble pressure method, Wilheimy plate method, DuNouy ring method, and oscillating jet method, etc. Most of these methods are only suitable for measuring interfacial tension higher than 1 mN/m, and only a few techniques are available for measuring ultralow interfacial tension (IFT). They are spinning drop, laser light scattering, and droplet deformation methods.

For the pendant drop method, the pendant drop created has to have an equator, i.e. the interfacial tension measured is limited to a value higher than 1 mN/m. Recently, Satherley et al. [J. Colloid Interf. Sci., 136, 574 (1990)] utilized the inflection plane of the pendant drop method to measure ultralow IFT and found that the method is suitable for pendant drops without an equator but still having an inflection plane.

SUMMARY OF THE INVENTION

The present invention provides an interfacial tension measuring system for a pendant drop having an equator or no equator, which is capable of measuring an interfacial tension lower than $10^{-2}$ mN/m.

The present invention also discloses a method of measuring interfacial tension by pendant drop digitization, in which a pendant drop created may either have an equator or have no equator. The method comprises the following steps:

1) forming a pendant drop of a second phase fluid in a first phase fluid and creating a silhouette of said pendant drop;
2) taking an, video image of said silhouette and digitizing said video image such that the loci of a plurality of points at the boundary of said silhouette are obtained;
3) calculating a theoretical curve of the boundary of said silhouette which comprises the following steps:

a) setting values of $X_0$, $Z_0$, $R_0$ and B, wherein $X_0$ and $Z_0$ are the loci of the apex of said silhouette in the horizontal and vertical directions respectively, $R_0$ is the radius of curvature at the apex, and B is the capillary constant and is defined by $$B = \Delta\rho g R_0^2 / \gamma$$

wherein $\Delta\rho$ is the density difference between the fluid phases, g is the gravitational acceleration constant, and $\gamma$ is the interfacial tension; and b) integrating the following equations:

$$\frac{d\phi}{ds'} = 2 + Bz' - \frac{\sin\phi}{x'}$$

$$\frac{dx'}{ds'} = \cos\phi$$

$$\frac{dz'}{ds'} = \sin\phi$$

with the boundary conditions: $x'(0)=z'(0)=s(0)=0$, wherein $x'=x/R_0$, $z'=z/R_0$, $s'=s/R_0$; x and z are the loci in the horizontal and vertical directions, s is the arc length measured from the apex, and $\psi$ is the turning angle measured from a horizontal axis;

4) calculating the normal distances between said theoretical curve of step 3) and said a plurality of points at the boundary of said silhouette; and 5) repeating steps 3) and 4) until the sum of the squares of said normal distances is less than a desired value, and computing $\gamma = \Delta\rho g R_0^2 / B$ by using the $R_0$ and B values set in step 3);

wherein the improvement comprises the initial $R_0$ and B values are set by the following steps:

I) selecting two points $P_2$ and $P_1$ from said a plurality of points in step 2), wherein the loci of the $P_2$ and $P_1$ are $(X_1, Z_1)$ and $(X_2, Z_2)$ respectively, and $X_1/Z_1 = A_1$, $X_2/Z_2 = A_2$, $A_1 > A_2$; and II) calculating $R_0$ and B values in accordance with the following equations:

$$y = a_0 + a_1 w + a_2 w^2 + a_3 w^3 + a_4 w^4 + a_5 w^5$$

$$y' = b_0 + b_1 w + b_2 w^2 + b_3 w^3$$

wherein $y = B$; $y' = X_2/R_0^2$; $w = X_1/X_2$; $a_0$, $a_1$, $a_2$, $a_3$, $a_4$ and $a_5$ are constants; and $b_0$, $b_1$, $b_2$ and $b_3$ are constants.

DETAILED DESCRIPTION OF THE INVENTION

The classical Laplace equation relates the pressure difference across a curved interface between a pendant drop of a second phase fluid and a first phase fluid $$\gamma\left(\frac{1}{R1} + \frac{1}{R2}\right) \quad (1)$$

where $\gamma$ is the interfacial tension, R1 and R2 are the two principal radii of curvature of the interface, and $\Delta P$ is the pressure difference across the interface.

The pressure difference between any point in the two-phase fluid system and the apex of the pendant drop can be expressed as follows by including the gravity head:

$$\Delta P = \Delta P_0 + \Delta\rho g z \quad (2)$$

wherein $\Delta P_0$ is the pressure difference across the interface at the apex of the pendant drop, and is equal to $2\gamma/R_0$ by replacing R1 and R2 in eq. 1 with $R_0$ which is the radius of curvature at the apex, $\Delta\rho$ is the density difference between the fluid phases, g is the gravitational acceleration constant, and z is the vertical distance between said any point and the apex.

Figure 1:
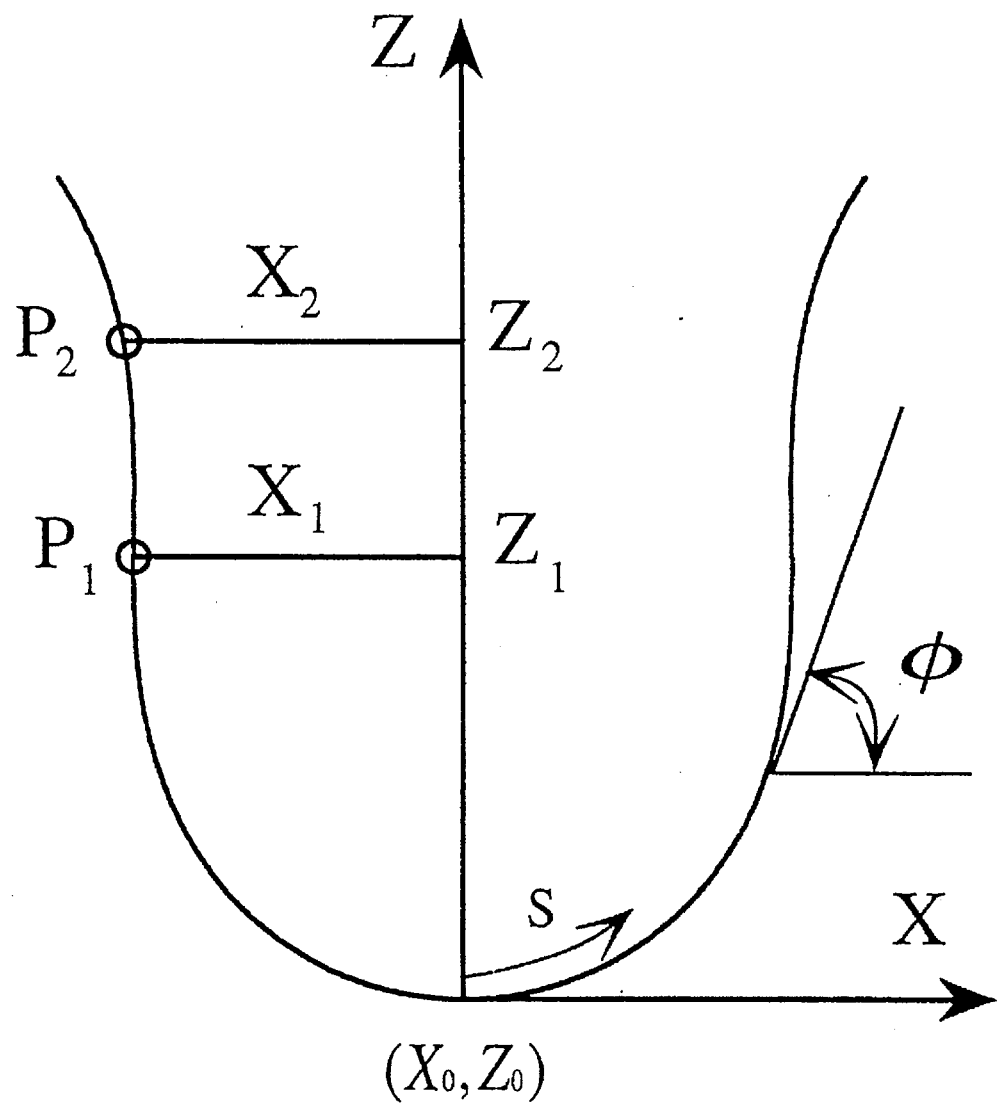
FIG. 1 shows a coordinate system of pendant drop and two selected interfacial loci $P_1$ $(X_1, Z_1)$ and $P_2$ $(X_2, Z_2)$.

Referring to FIG. 1, a two dimensional (x, z) coordinate system is used to express the spatial positions of the curved interface, and the following equations can be derived from plane geometry $$\frac{dx}{ds} = \cos\phi, \quad \frac{dz}{ds} = \sin\phi \quad (3)$$

$$\frac{1}{R1} = \frac{d\phi}{ds}, \quad \frac{1}{R2} = \frac{\sin\phi}{x} \quad (4)$$

wherein x and z are the horizontal and vertical spatial positions respectively, s is the arc length measured from the apex, and $\psi$ is the turning angle measured from a horizontal axis.

Substituting eqs. (2), (3) and (4) into eq. 1, the Laplace equation (1) will have the following form:

$$\frac{d\phi}{ds} = \frac{2}{R2} + \frac{\Delta\rho g z}{\gamma} - \frac{\sin\phi}{x} \quad (5)$$

Using the dimensionless variables $s'=s/R_0$, $x'=x/R_0$, $z'=z/R_0$, the eqs. (3) and (5) are converted to the following form:

$$\frac{d\phi}{ds'} = 2 + Bz' - \frac{\sin\phi}{x'} \quad (7)$$

$$\frac{dx'}{ds'} = \cos\phi \quad (8)$$

-continued $$\frac{dz'}{ds'} = \sin\phi \quad (9)$$

Figure 2:
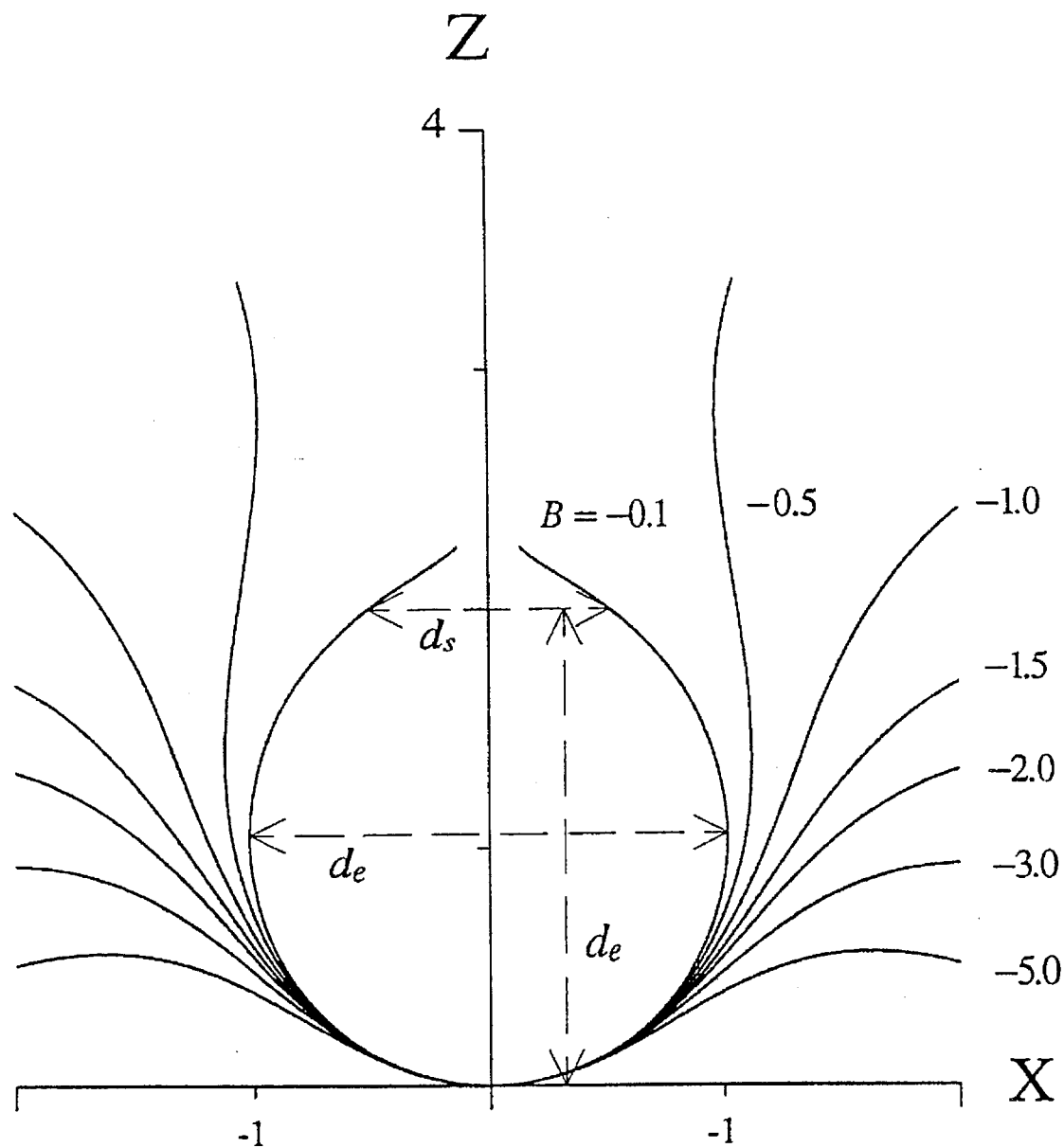
FIG. 2 shows pendant drop profiles calculated from eqs. (7)–(9) for different values of capillary constant B ($R_0=1$).

The equations (7)–(9) are subject to the boundary conditions x'(0)=z'(0)=s(0)=0. Equations (7)–(9) can be integrated numerically, such as a fourth-order Runge-Kutta scheme [Carnahan, B; Luther, H. A.; Wilkes, J. O. Applied Numerical Methods; John Wiley & Sons: New York, 1969] initialized with an approximate solution [Huh, C.; Reed, R. L. J. of Colloid Interface Sci. 1983, 91,472]

$$z' = \frac{2}{-B} [1 - J_0(\sqrt{-B}\ x')]$$

which is valid near the apex where $\phi \ll 1$. Here $J_0(x')$ is the Bessel function of the first kind. The pendant drop profiles calculated from eqs. (7)–(9) for different values of capillary constant (B) and $R_0=1$ are shown in FIG. 2.

In the present invention, video images of the silhouettes of pendant drops are digitized to determined the interface loci. These loci are then compared with theoretical interfacial shapes generated by the solution of the eqs. (7)–(9). The interfacial tension is then determined once an optimum congruence is achieved between the theoretical shape and the experimental loci. To serve this purpose, an objective function is defined as the sum of squares of the normal distance (dn) between the measured points $U_n$ and the calculated curve v, i.e.

$$E = \sum_{n-1}^{N} [dn(U_n, v)]^2,$$

N is the total number of experimental points. The objective function depends on four unknown parameters: the actual location of the apex ($X_0$ and $Z_0$), the radius of curvature at apex ($R_0$), and the capillary constant (B). To obtain the optimum congruence between the theoretical curve and the data points, the objective function is minimized with respect to the four parameters ($\partial E/\partial q_i 0$, i=1, 2, 3, 4). Minimization equations are solved by applying directly the Newton-Raphson method [Carnahan, B; Luther, H. A.; Wilkes, J. O. Applied Numerical Methods; John Wiley & Sons: New York, 1969], and from the optimum values of $R_0$ and B the tension $\gamma$ can be computed.

The success of the fitting relies on a set of initial guesses of four parameters. The Newton-Raphson method will not provide a congruent result if the initial guesses are far away from the actual values. Initial guesses for the Newton-Raphson method procedure are obtained in the following way: $X_0$ is initially guessed as the centroid of the 100–500× location data points, and $Z_0$ as the average of the three lowest (or the highest) z coordinates. The values of B and $R_0$ from the classical selected plane technique of pendant drop method are usually used as the initial guess of the numerical calculation if the pendant drop has an equator. Unfortunately, pendant drops of ultralow interfacial tension have no equator because the value of capillary constant B is usually less than −0.6066, a critical value for equator formation, when $\gamma$ is very small. A new method is developed in the present invention to obtain an accurate initial guess for B and $R_0$.

Referring to FIG. 1, two interfacial loci, $P_1=(X_1, Z_1)$ and $P_2=(X_2, Z_2)$ on the profile of drop are selected from the raw data. Here, $X_1$, $X_2$ and $Z_1$, $Z_2$ are the distances of $P_1$, $P_2$ away from the apex of the drop in x direction and in z direction, respectively. Define a function of drop shape $X_{A1}$ as the value of $X_1/R_0$ of interfacial locus $P_1$ in which the ratio of $X_1/R_0$ to $Z_1/R_0$ is equal to A1 (i.e., $X_1/Z_1=A1$).

Figure 3A:
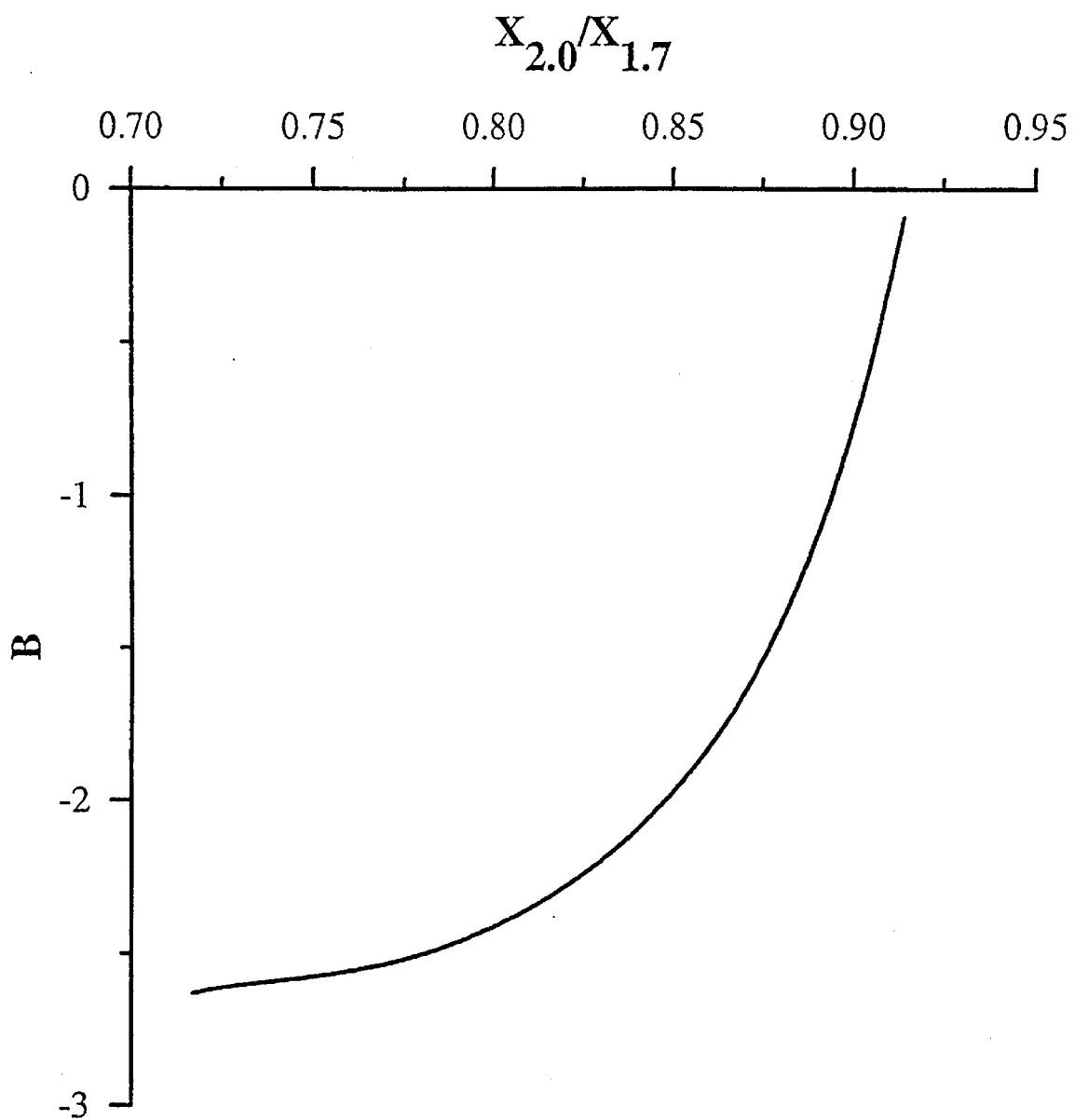
FIG. 3a is a plot which shows a representative relationship of capillary constant B versus $X_{A1}/X_{A2}$ (A1=2.0, A2=1.7).
Figure 3B:
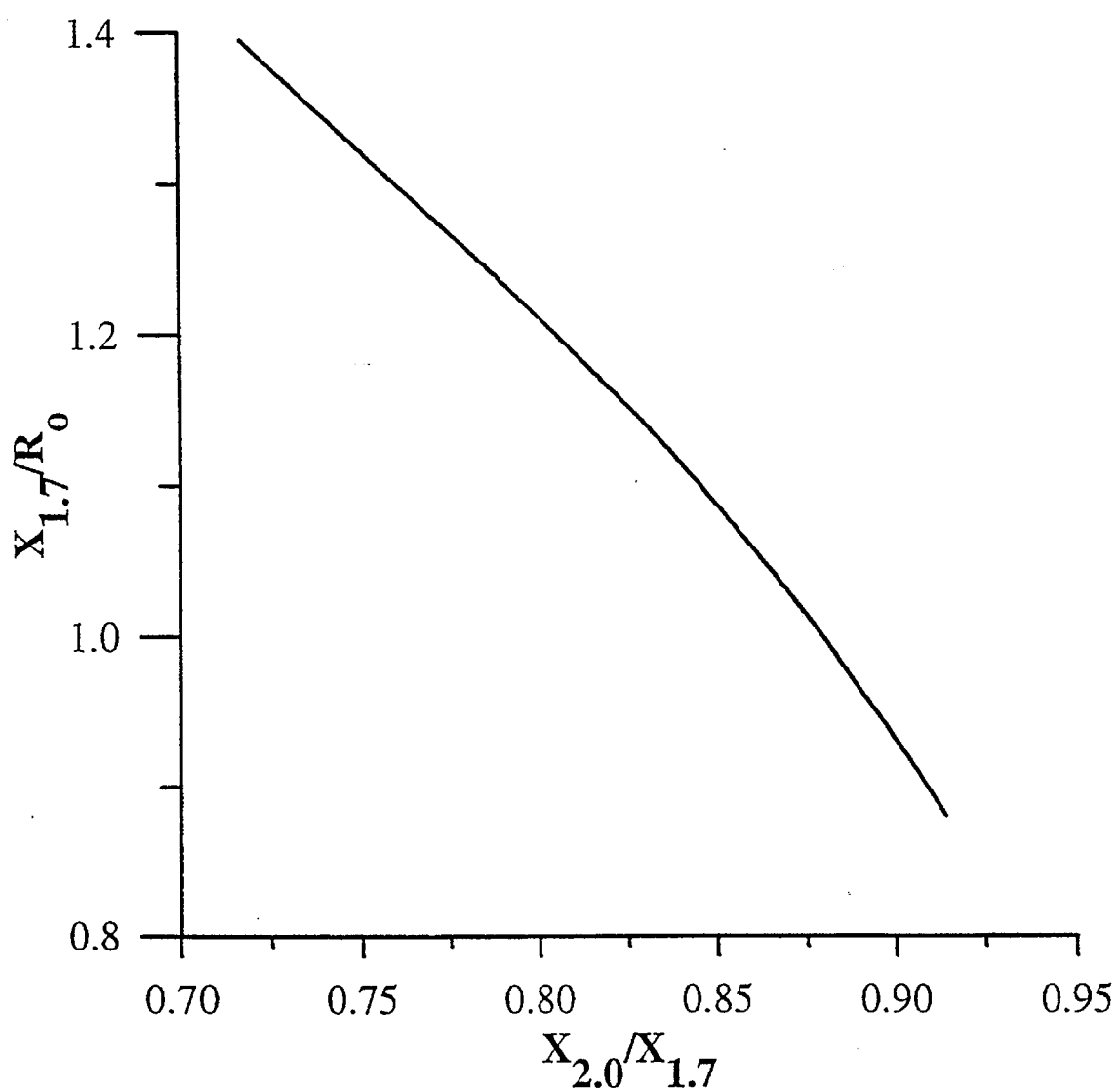
FIG. 3b is a plot which shows a representative relationship of $X_{A2}/R_0$ versus $X_{A1}/X_{A2}$ (A1=2.0, A2=1.7).

Similarly, $X_{A2}$ is the value $X_2/R_0$ of point $P_2$ in which $X_2/Z_2=A2$. The value of A1 has to be greater than the value of A2. By integrating eqs. (7)–(9) for different values of B, graphs can be constructed of B as a function of $X_{A1}/X_2$, and $X_{A2}/R_0$ as a function of $X_{A1}/X_{A2}$. Two typical curves are shown in FIGS. 3A and 3B, and the best fits of the curves can be described by the following polynomial equations:

$$y=a_0+a_1w+a_2w^2+a_3w^3+a_4w^4+a_5w^5$$

$$y'=b_0+b_1w+b_2w^2+b_3w^3$$

wherein $y=B$; $y'=X_{A2}/R_0 32 X_2/R_0^2$; $w=X_{A1}/X_{A2}=X_1/X_2$; $a_0$, $a_1$, $a_2$, $a_3$, $a_4$, $a_5$, $b_0$, $b_1$, $b_2$ and $b_3$ are all constants, and their values are summarized in Tables 1 and 2.

TABLE 1

| A1 | A2 | $a_0$ | $a_1$ | $a_2$ | $a_3$ | $a_4$ | $a_5$ |
|---|---|---|---|---|---|---|---|
| 2.6 | 2.0 | −1626.14 | 11751.4 | −34035.5 | 49310.8 | −35771.3 | 10409.5 |
| 2.4 | 1.9 | −2395.11 | 16662.5 | −46419.2 | 264678.1 | −45103. | 12605.9 |
| 2.2 | 1.8 | −3670.3 | 24601 | −65982.5 | 88478.8 | 59345.6 | 15938.6 |
| 2.0 | 1.7 | 8974.58 | 56893.8 | −144270 | 182899 | −115951 | 29416.7 |
| 1.9 | 1.6 | −6963.1 | 44147.9 | −111979 | 142015 | −90078.4 | 22868.8 |
| 1.7 | 1.5 | −21314.3 | 128041 | −307588 | 369346 | −221716 | 53236.7 |
| 1.6 | 1.4 | −11315.7 | 68957.7 | −167992 | 204500 | −124414 | 302688 |
| 1.5 | 1.3 | −9511.74 | 57511.9 | −139051 | 168036 | −101511 | 24529.7 |
| 1.4 | 1.2 | −6030.26 | 36571 | −88680.5 | 107469 | −65101.9 | 15775.2 |
| 1.3 | 1.1 | −5849.68 | 34740 | −82536.6 | 98052.6 | −58258.8 | 13853.7 |
| 1.2 | 1.0 | −4319.99 | 25338.8 | −59473.4 | 69817.1 | −41002.6 | 9640.63 |
| 1.1 | 0.9 | −2658.5 | 154499 | −35937.5 | 41815.1 | −24345.4 | 5676.44 |
| 1.0 | 0.8 | −1256.08 | 7291.7 | −16943.2 | 19689.6 | −11448.5 | 2666.19 |
| 0.9 | 0.7 | −793.293 | 4481.15 | −10139.5 | 11479.7 | −6506.96 | 1478.41 |
| 0.8 | 0.6 | −209.629 | 903.934 | −1459.58 | 1050.7 | −284.841 | 0.0 |
| 0.7 | 0.5 | 131.891 | −540.282 | 828.438 | −567.048 | 146.405 | 0.0 |

TABLE 2

| A1 | A2 | $b_0$ | $b_1$ | $b_2$ | $b_3$ |
|---|---|---|---|---|---|
| 2.6 | 2.0 | 5.11827 | 13.1869 | 16.014 | −7.67093 |
| 2.4 | 1.9 | 5.9591 | −161208 | 19886 | −9.39301 |
| 2.2 | 1.8 | 7.45975 | −21.5532 | 26.9509 | −12.4603 |
| 2.0 | 1.7 | 11.6447 | 36.8397 | 46.0846 | −20.421 |
| 1.9 | 1.6 | 10.9226 | −.3.3751 | 41.974 | 18.6345 |
| 1.7 | 1.5 | 22.826 | −76.2272 | 93.0061 | −39.0033 |
| 1.6 | 1.4 | 18.0622 | −59.0632 | 72.6021 | −30.9398 |
| 1.5 | 1.3 | 17.2787 | −55.5056 | 67.6441 | −28.6989 |
| 1.4 | 1.2 | 14.7532 | −45.9503 | 55.786 | −23.8047 |
| 1.3 | 1.1 | 14.3806 | −43.6934 | 52.1208 | −21.9556 |
| 1.2 | 1.0 | 12.587 | −36.6253 | 42.9993 | −18.0342 |
| 1.1 | 0.9 | 10.4786 | −28.6232 | 32.914 | −13.771 |
| 1.0 | 0.8 | 8.45713 | −21.1048 | 23.531 | −9.81688 |
| 0.9 | 0.7 | 6.96068 | −15.5578 | 16.513 | −6.79252 |
| 0.8 | 0.6 | 5.0581 | −9.16653 | 9.01466 | −3.7449 |
| 0.7 | 0.5 | 13.37873 | −4.07614 | 3.40158 | −1.53363 |

As values of A1 and A2 are selected, $P_1$, $P_2$, $X_1$, $X_2$, $Z_1$ and $Z_2$ are known from the raw data, and therefore the initial guesses of B and $R_0$ can be obtained.

From above, a method of measuring interfacial tension embodied in accordance with the present invention comprises the following steps:

1) forming a pendant drop of a second phase fluid in a first phase fluid and creating a silhouette of said pendant drop;

2) taking an video image of said silhouette and digitizing said video image such that the loci of a plurality of points at the boundary of said silhouette are obtained;

3) calculating a theoretical curve of the boundary of said silhouette which comprises the following steps:

a) setting values of $X_0$, $Z_0$, $R_0$ and B, wherein $X_0$ and $Z_0$ are the loci of the apex of said silhouette in the horizontal and vertical directions respectively, $R_0$ is the radius of curvature at the apex, and B is the capillary constant and is defined by $$B=\Delta\rho g R_0^2/\gamma$$

wherein $\Delta\rho$ is the density difference between the fluid phases, g is the gravitational acceleration constant, and $\gamma$ is the interfacial tension; and b) integrating the following equations:

$$\frac{d\phi}{ds'} = 2 + Bz' - \frac{\sin\phi}{x'}$$

$$\frac{dx'}{ds'} = \cos\phi$$

$$\frac{dz'}{ds'} = \sin\phi$$

with the boundary conditions: $x'(0)=z'(0)=s(0)=0$, wherein $x'=x/R_0$, $z'=z/R_0$, $s'=s/R_0$; x and z are the loci in the horizontal and vertical directions, s is the arc length measured from the apex, and $\psi$ is the turning angle measured from a horizontal axis;

4) calculating the normal distances between said theoretical curve of step 3) and said a plurality of points at the boundary of said silhouette; and 5) repeating steps 3) and 4) until the sum of the squares of said normal distances is less than a desired value, and computing $\gamma=\Delta\rho g R_0^2/B$ by using the $R_0$ and B values set in step 3);

wherein the improvement comprises the initial $R_0$ and B values are set by the following steps:

I) selecting two points $P_2$ and $P_1$ from said a plurality of points in step 2), wherein the loci of the $P_2$ and $P_1$ are $(X_1, Z_1)$ and $(X_2, Z_2)$ respectively, and $X_1/Z_1=A_1$, $X_2/Z_2=A_2$, $A_1>A_2$; and II) calculating $R_0$ and B values in accordance with the following equations:

$$y = a_0 + a_1 w + a_2 w^2 + a_3 w^3 + a_4 w^4 + a_5 w^5$$

$$y' = b_0 + b_1 w + b_2 w^2 + b_3 w^3$$

wherein y=B; $y'=X_2/R_0^2$; $w=X_1/X_2$; $a_0$, $a_1$, $a_2$, $a_3$, $a_4$ and $a_5$ are constants listed in Table 1; and $b_0$, $b_1$, $b_2$ and $b_3$ are constants listed in Table 2.

In one of the preferred embodiments of the present invention, two main computer programs PA and PB were written to perform the tasks of calculating the theoretical curve in step 3), and obtaining the optimum congruence between the theoretical curve and the data points in steps 4) and 5), respectively. Three to seven iterations are necessary for the program PB to converge, and the standard deviation of the distance between a measured point and the calculated curve is usually less than 0.1 pixel (about 1 µm). Note that there are many sets of A1 and A2 can be used to obtain the values of B and $R_0$. It can be seen from FIG. 2 that the theoretical curves for B less than about −0.6 does not have an equator ($d_e$) and they depart further from one another at points further from the apex. Therefore, the initial guess values of B and $R_0$ obtained by this method will be more accurate if $P_1$ and $P_2$ closer to the liquid-liquid-solid contact circle are selected.

A suitable system for embodying the present method was disclosed in two articles published by one of the present inventors, Shi-Yow Lin, and his coworkers [Lin, S. Y.; McKeigue, K.; Maldarelli, C. AIChE J. 1990, 36, 1785; and Lin, S. Y.; McKeigue, K.; Maldarelli, C. Langmuir 1991, 7, 1055], and the disclosure thereof is incorporated by reference. This system is capable of measuring the interfacial tension dynamically.

Figure 4:
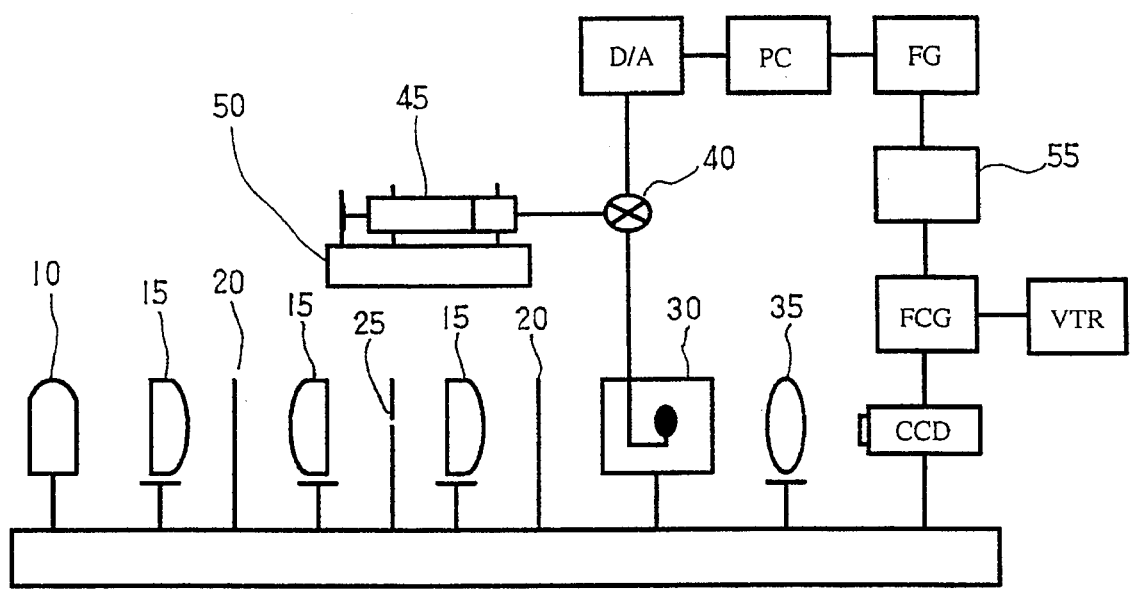
FIG. 4 is a schematic diagram which shows a pendant drop tensiometry apparatus and the video digitization equipment.

The equipment shown in FIG. 4 is used to create a silhouette of a pendant drop, to video image the silhouette, to digitize the image of a pendant drop, and to compute the interfacial tension. As shown in FIG. 4, the image forming and recording system consists of a light source 10 (a halogen lamp with constant light intensity; a plano-convex lens system for producing a collimated beam including plano-convex lens 15, filters 20, and a pinhole 25; a quartz cell enclosed in a thermostatic air chamber 30; an objective lens 35 (effective local length 60 mm, f/# 7.1); a solid-state video camera CCD (MS-4030 CCD, Sierra, Scientific Co.); and a video recorder VTR (VO-9600, Sony) with a frame code generator FCG (FCG-700, Sony) which is connected to the solid-state video camera CCD. The output signal of the frame code generator FCG is transmitted to a monitor 55 and a videoimage digitizer FG (DT2861 Arithmetic Frame Grabber, Data Translation). The videoimage digitizer FG digitizes picture into 480 lines×512 pixels and assigns to each one a level of gray with eight-bit resolution, and then the digitized image data are transferred to the personal computer PC in which the data are recorded and compared with the calculated theoretical curves.

The drop-forming system consists of a stainless steel (inverted) needle, 22 gauge (0.016 in. i.d.; 0.028 in. o.d.) or 16 gauge (0.047 in. i.d.; 0.065 in. o.d.), which is connected to the normally closed port of a three-way miniature solenoid valve 40. The common port of the valve 40 is connected to a syringe 45 placed in a syringe pump 50. The valve 40 is controlled by the output signal of a D/A card which is connected to a personal computer PC.

An edge detection routine is devised to locate the interface contour from the digitized image, and a calibration procedure using stainless steel balls (1.577±0.002 mm and 1.983±0.002 mm, calibrated by a digital linear gauge, PDN-12N, Ozaki Mfg. Co.) is applied to determine the distance between pixels along a row and along a column. The calibration procedure yields values of 100.86 pixels/mm horizontally and 124.56 pixels/mm vertically.

EXAMPLES n-Tetradecane (purity 99+%) was obtained from Tokyo Kasei Chemical Co.. Nonionic surfactant $C_6E_2$ (diethylene glycol monohexylether, purity 99%) was purchased from Aldrich Chemical Co. Aerosol OT (dioctyl sodium sulfosuccinate, 99%) was from Sigma Chemical Co. Heptane (>99% purity) and sodium chloride (99.5% purity) were from Merck. Acetone (HPLC grade) used to verify for the tension measurement was obtained from Fisher Scientific Co. These Chemicals were used as received without further purification. Water was purified via a Barnstead NANOpure II water purification system, with the output water having a specific conductance less than 0.057 $\mu\Omega^{-1}$/cm. The values of the surface tension of air/water and air/acetone are 72.3±0.1 and 23.2±0.1 mN/m respectively at 22.70°±0.02° C.

The mixtures were prepared in a flask and placed in a water thermostat, whose temperature stability was ±0.1° C., for several days to allow the system to reach equilibrium. Before and during the equilibrium process, the samples were shaken vigorously several times to ensure a through mixing. After equilibrium was reached, all three phases were transparent with sharp, mirror-like interfaces. Following equilibration, three liquid phases were carefully removed by using syringe and put into a quartz cell of 4.6×4.1×4.3 cm inside. Next, this cell with a cover was placed in an air thermostat for several hours, sometimes up to 72 h, to ensure the equilibrium was reached after transferring the sample from the flask to the quartz cell. The temperature stability of the air thermostat chamber 30, which is part of the pendant drop tensiometry as shown in FIG. 4, is better than ±0.02° C. The density measurements of the solution were made by using a vibrating-tube densiometer (Anton Paar DMA 58).

The quartz cell was initially filled with the mixture, which includes α, β, and ω three phases from top to bottom, and placed in the air thermostat chamber 30 for several hours to ensure that the equilibrium was reached. The drop forming system (needle, valve, and connecting Teflon tubing) was also placed in the thermostat during this time. The tip of the needle was positioned in one of the liquid phase (e.g., ω phase). After some ω phase liquid had been sucked into the needle, the drop forming needle was then positioned in the path of the collimated light beam that was in the region of another liquid phase (e.g., β phase). The syringe pump 50 was turned on, and the liquid ω inside is allowed to pass through the needle, thereby forming a drop of ω phase inside the β liquid phase. The valve 40 was then closed by input from the keyboard of the personal computer PC. The drop so created is one of constant mass. The change in volume, as the interfacial tension relaxes, is only a few percent over a time period of several minutes. After the solenoid was closed and the drop was formed, sequential digital images were then taken of the drop, first at intervals of approximately 0.1 s, and then later in intervals of the order of seconds. After the interfacial tension relaxation was complete, the images were processed to determine the drop edge coordinates. An inverted needle was used when liquid drops of lower density were generated in another liquid phase of higher density.

The interfacial tension of pendant drops of β phase in α liquid phase (γβα) was measured by using different size of needle (16 and 22 gauge) at 25° C. Here, the drops generated by using a 16 gauge needle have no equator, but drops by a 22 gauge needle have equators. Pendant drops of α phase in β liquid phase were also taken to check the difference between $\gamma_{\alpha\beta}$ (drop of α in β liquid phase) and $\gamma_{\beta\alpha}$.

Figure 5A:
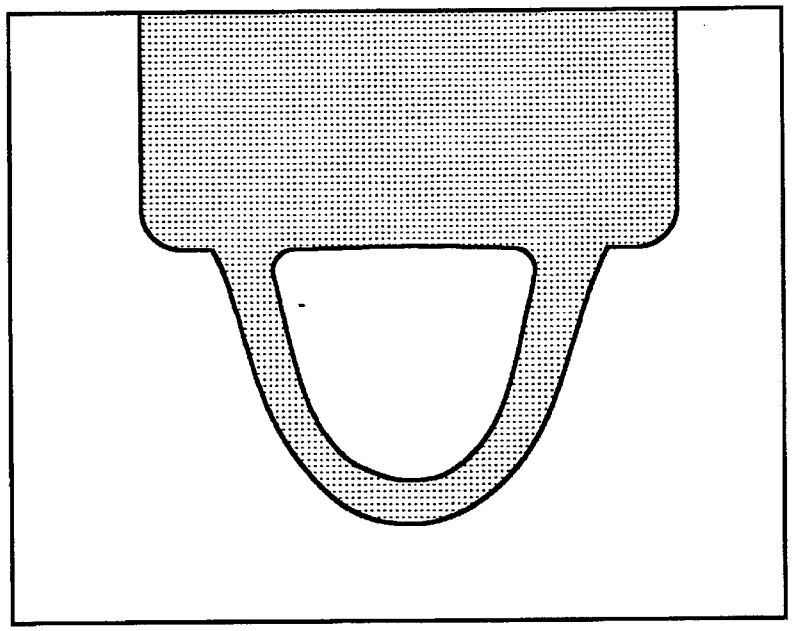
FIGS. 5a–5c show pendant drop images of water +n-tetradecane+$C_6E_2$ system at 25° C.: a) a drop image of β phase in α liquid phase by using a 16 gauge needle (0.047 in. i.d.; 0.065 in o.d.); b) a drop image of β phase in α liquid phase by using a 22 gauge needle (0.016 in. i.d.; 0.028 in. o.d.); and c) a drop image of α phase in β liquid phase by using an inverted 22 gauge needle.
Figure 5B:
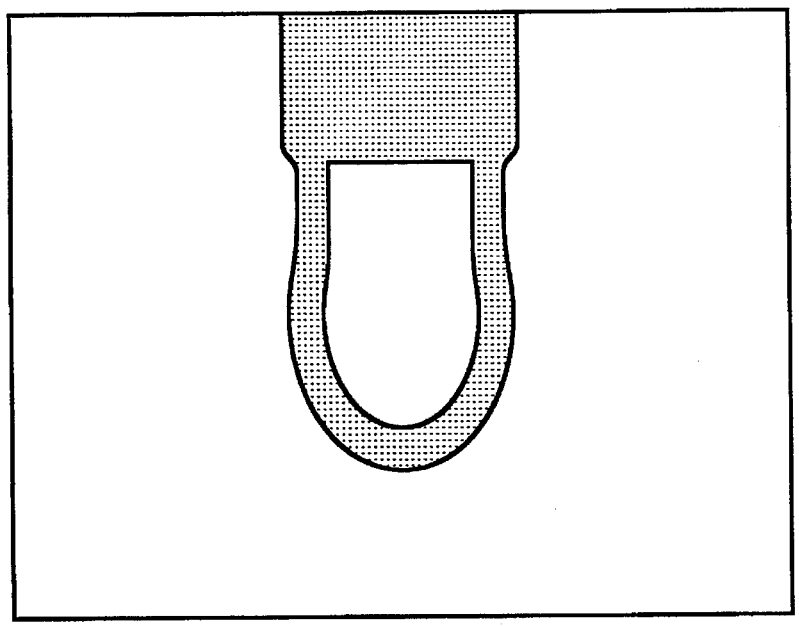

FIG. 5a shows a drop image of β phase in α liquid phase of water+n-tetradecane +$C_6E_2$ system at 25° C. by using a 16 gauge needle (0.047 in. i.d.; 0.065 in o.d.). The drop does not wet the stainless-steel needle and has no equator. The average IFT ($\gamma_{\beta\alpha}$) of drops using this needle is equal to 0.2848±0.0020 mN/m. FIG. 5b shows a drop image of β phase in α liquid phase by using a 22 gauge needle (0.016 in. i.d.; 0.028 in. o.d.). The drop, wetting the stainless-steel needle, has an equator and drops using this needle have an average IFT ($\gamma_{\beta\alpha}$) 0.2865±0.0026 mN/m. If a drop of α phase in β2 liquid phase is generated by using an inverted 22 gauge needle, the drop does not wet the needle but has an equator (see FIG. 5c). The average IFT ($\gamma_{\alpha\beta}$) of drops using this needle is equal to 0.2860±0.0046 mN/m. The results show that the interfacial tension measured by needles of different sizes agree well with each other. Moreover, the measured $\gamma_{\beta\alpha}$ and $\gamma_{\alpha\beta}$ are also very close.

Figure 5C:
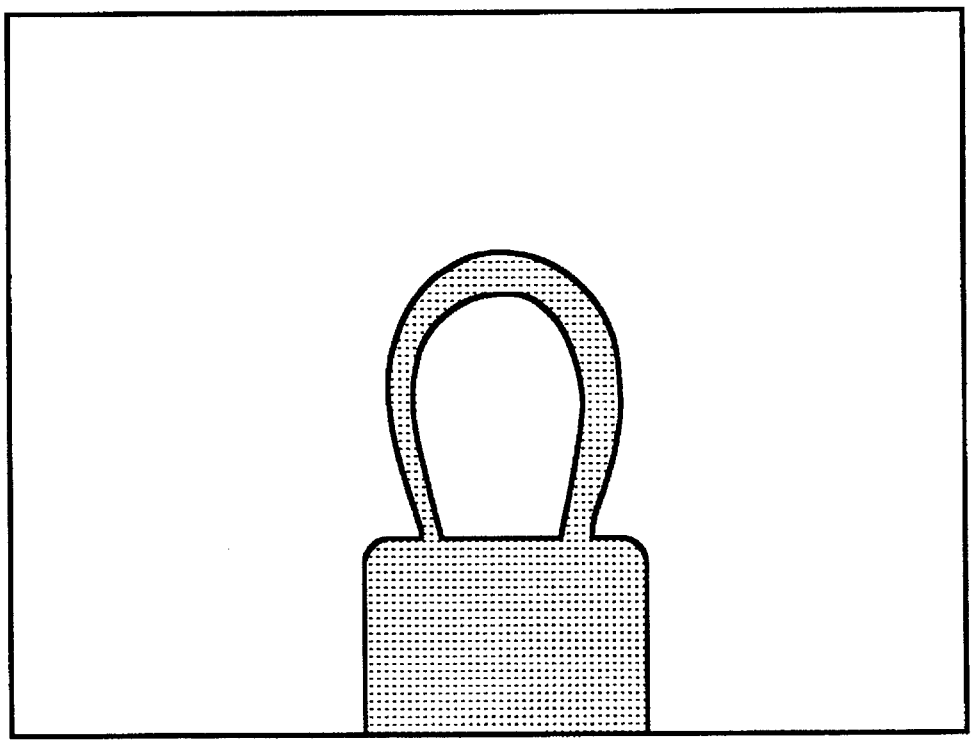
Figure 6A:
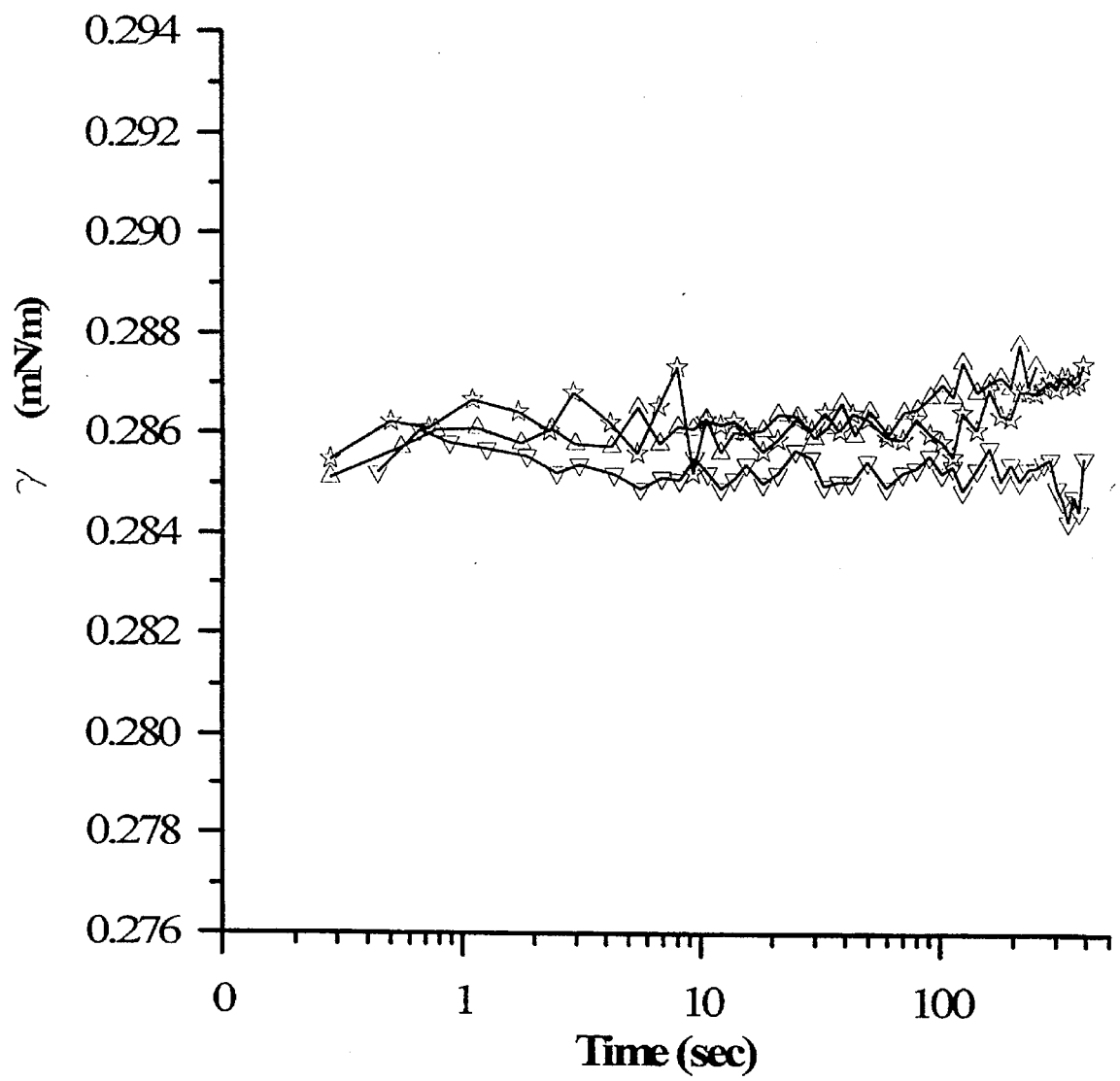
FIGS. 6a–6c show the dynamic IFT profiles for the pendant drops created in accordance with the procedures used in FIGS. 5a–5c, respectively, in which each different symbol represents a separate drop.
Figure 6B:
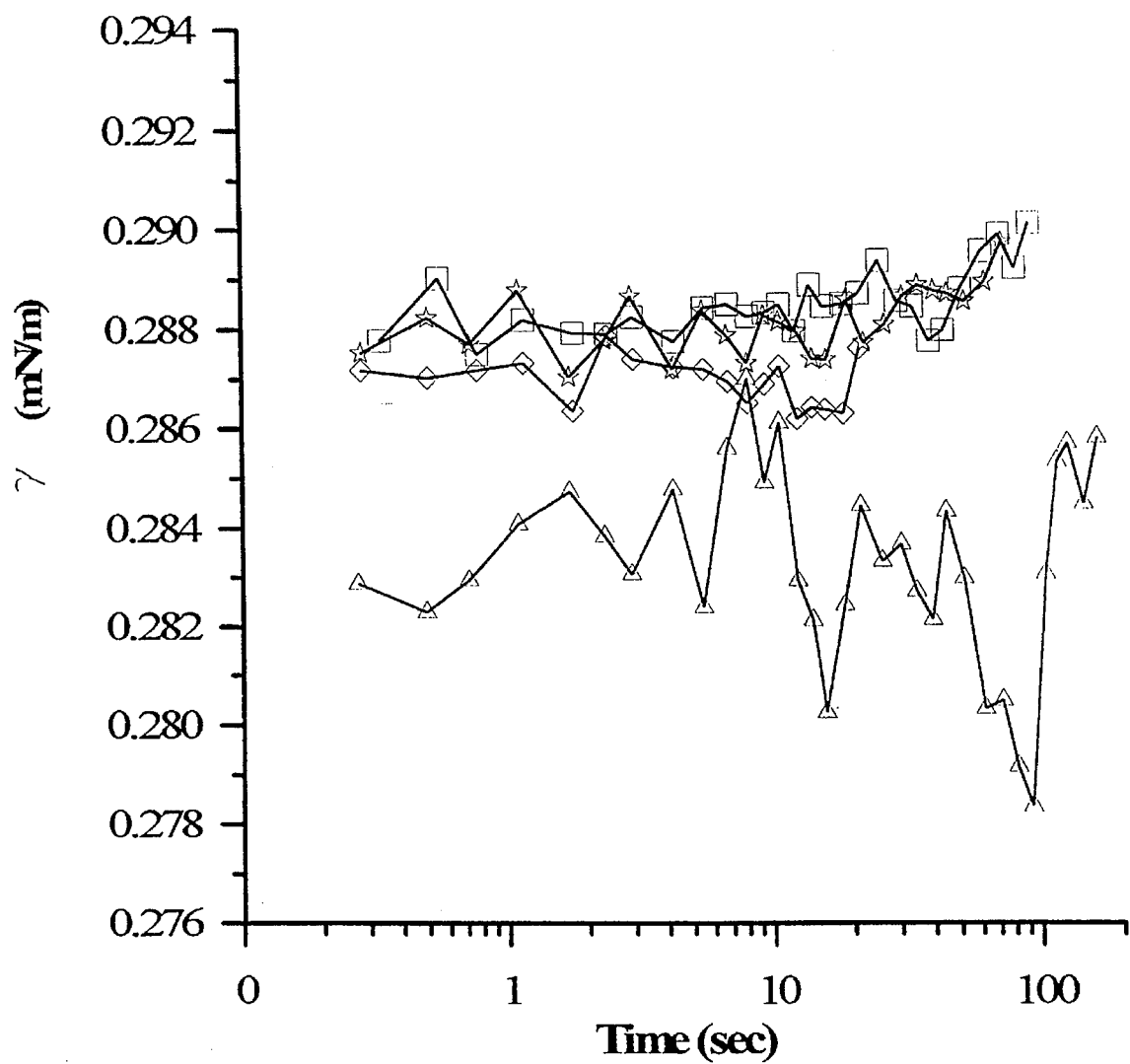
Figure 6C:
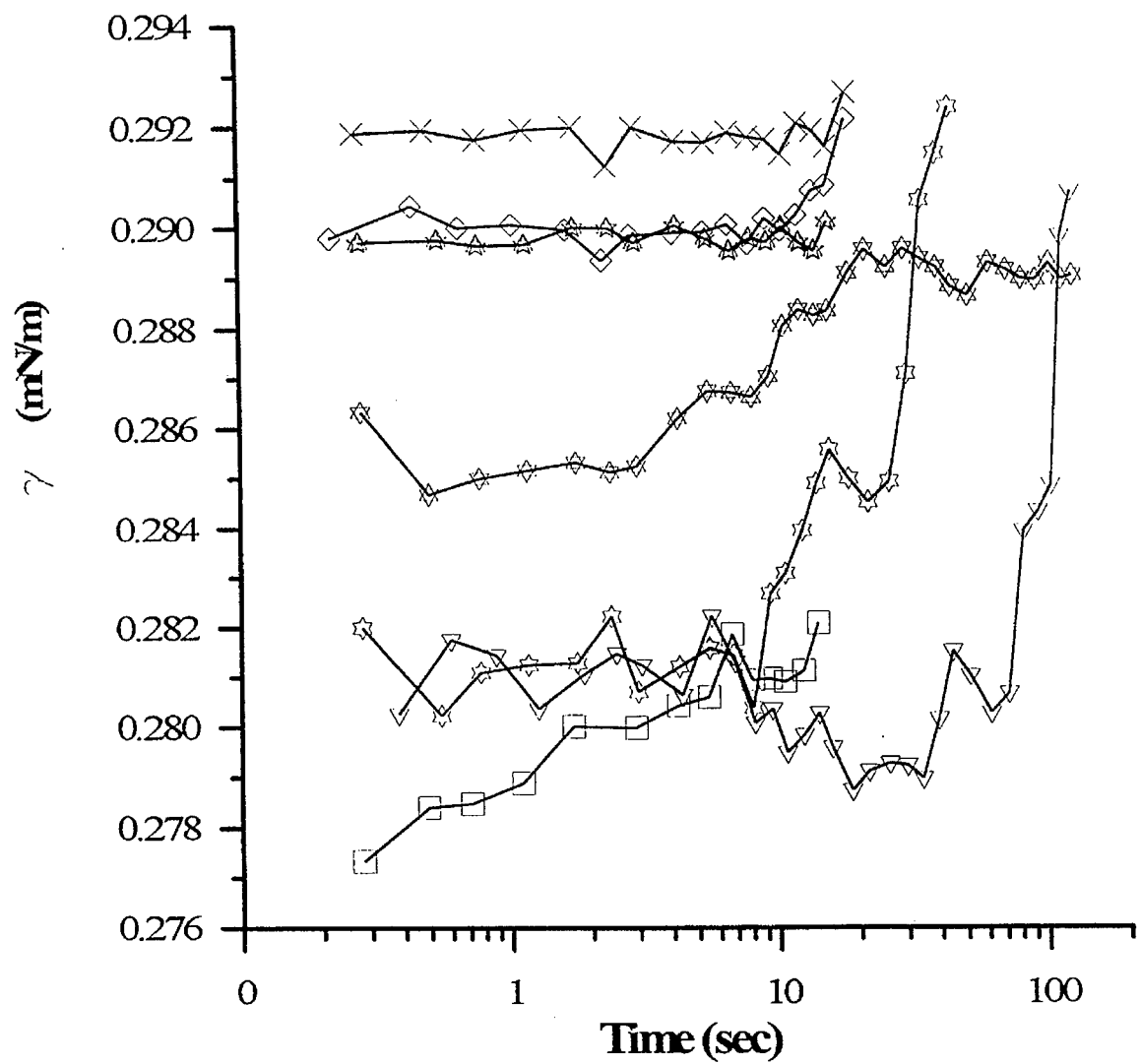

FIGS. 6a–6c show the dynamic IFT profiles for the pendant drops created in accordance with the procedures used in FIGS. 5a–5c, respectively, in which each different symbol represents a separate drop. It can be seen from FIGS. 6a–6c that the interfacial tension measured for the separate drops is more consistent in the case where the pendant drops have no equator (FIG. 6a) than in the cases where the pendant drops have a equator (FIGS. 6b–6c). Please note that the all the dynamic IFT profiles in FIGS. 6a–6c were obtained by using the present method. That is to say the present method is also capable of measuring interfacial tension of a pendant drop having an equator.

Figure 7A:
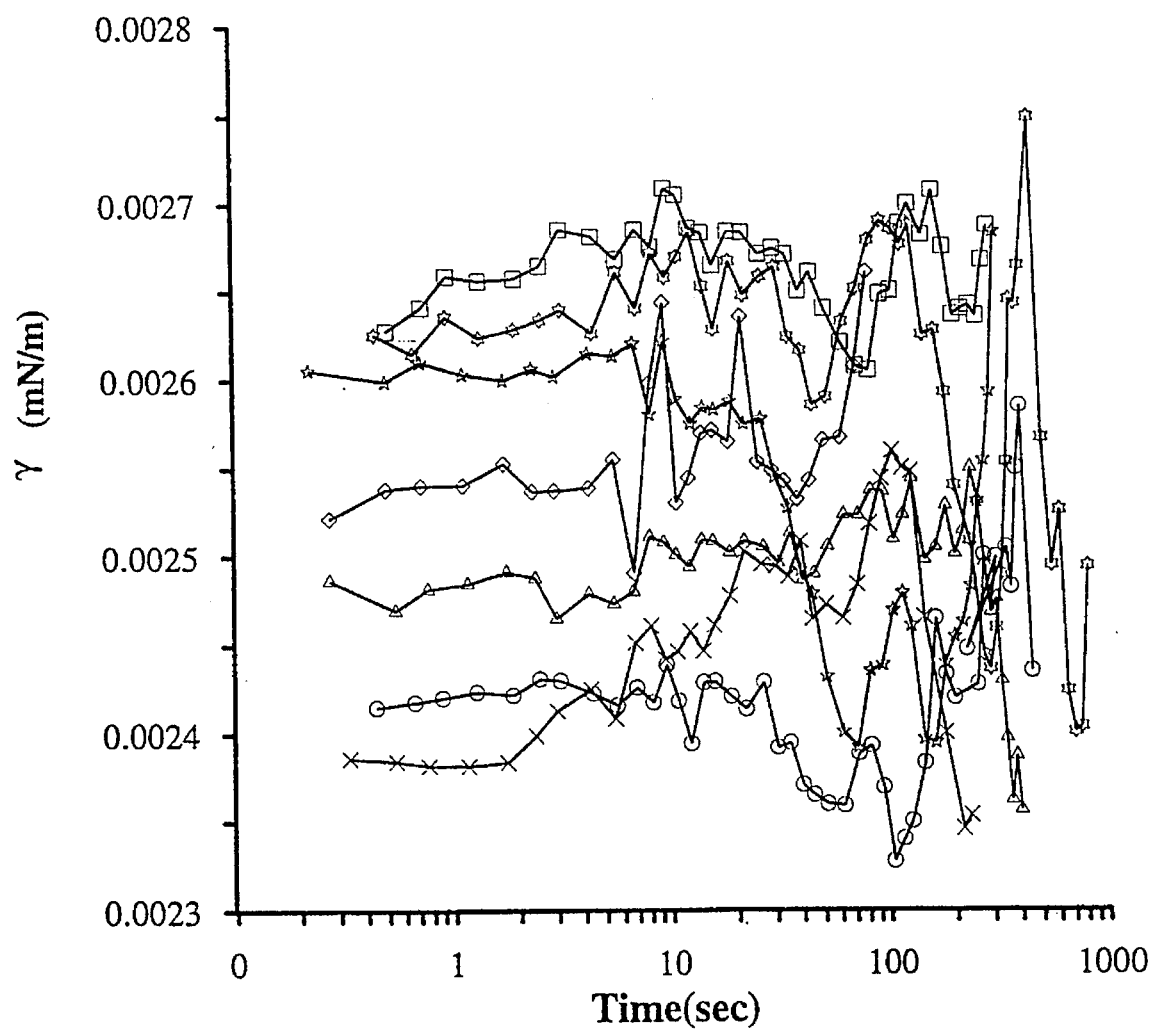
FIGS. 7a–7c show representative dynamic IFT profiles for the water+n-tetradecane+$C_6E_2$ three-coexisting-liquid-phase ternary system at 11.00°±0.02° C., in which each different symbol represents a separate drop, a) $\gamma_{\beta\omega}$; b) $\gamma_{\alpha\beta}$; and c) $\gamma_{\alpha\omega}$.
Figure 7B:
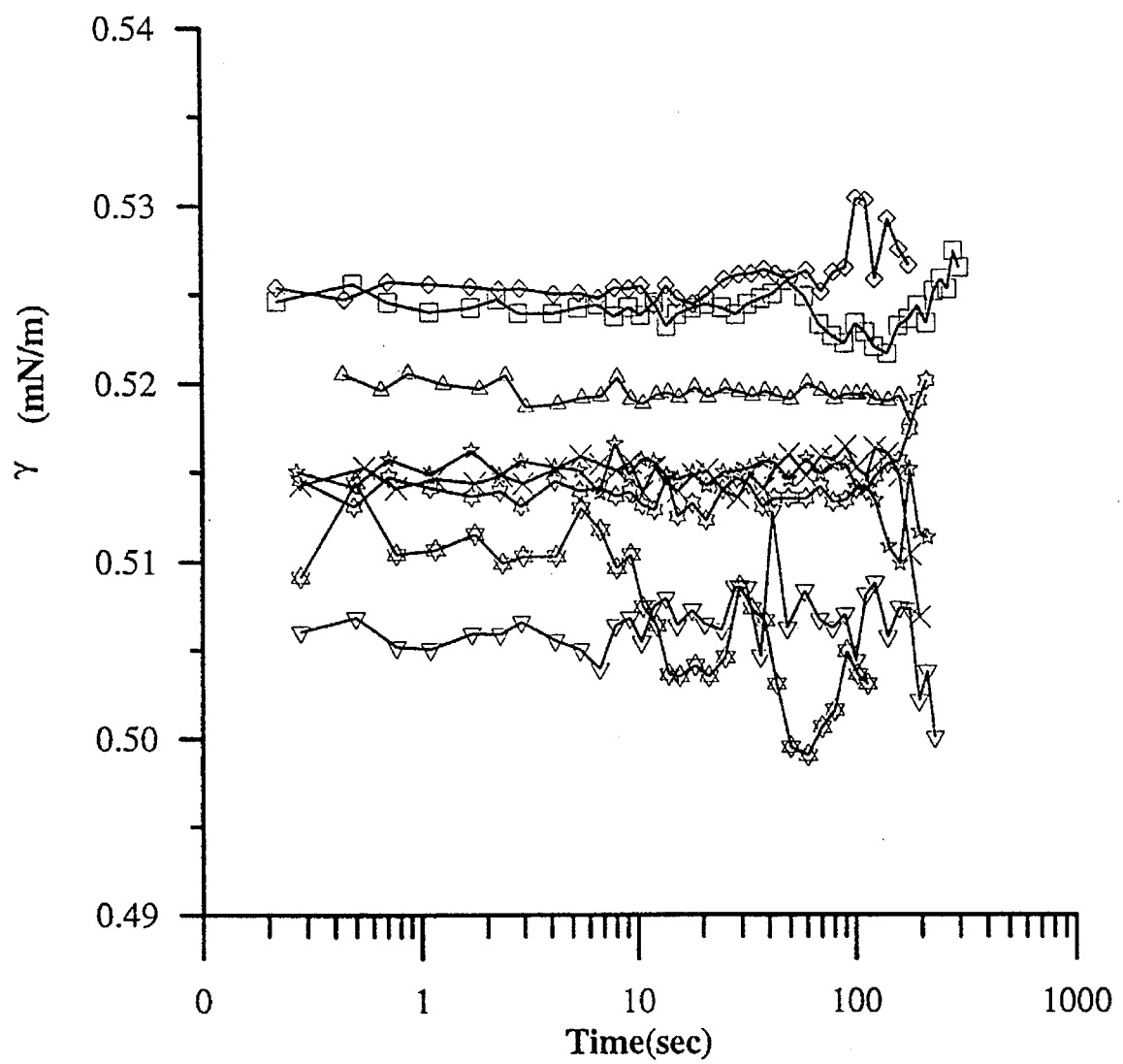
Figure 7C:
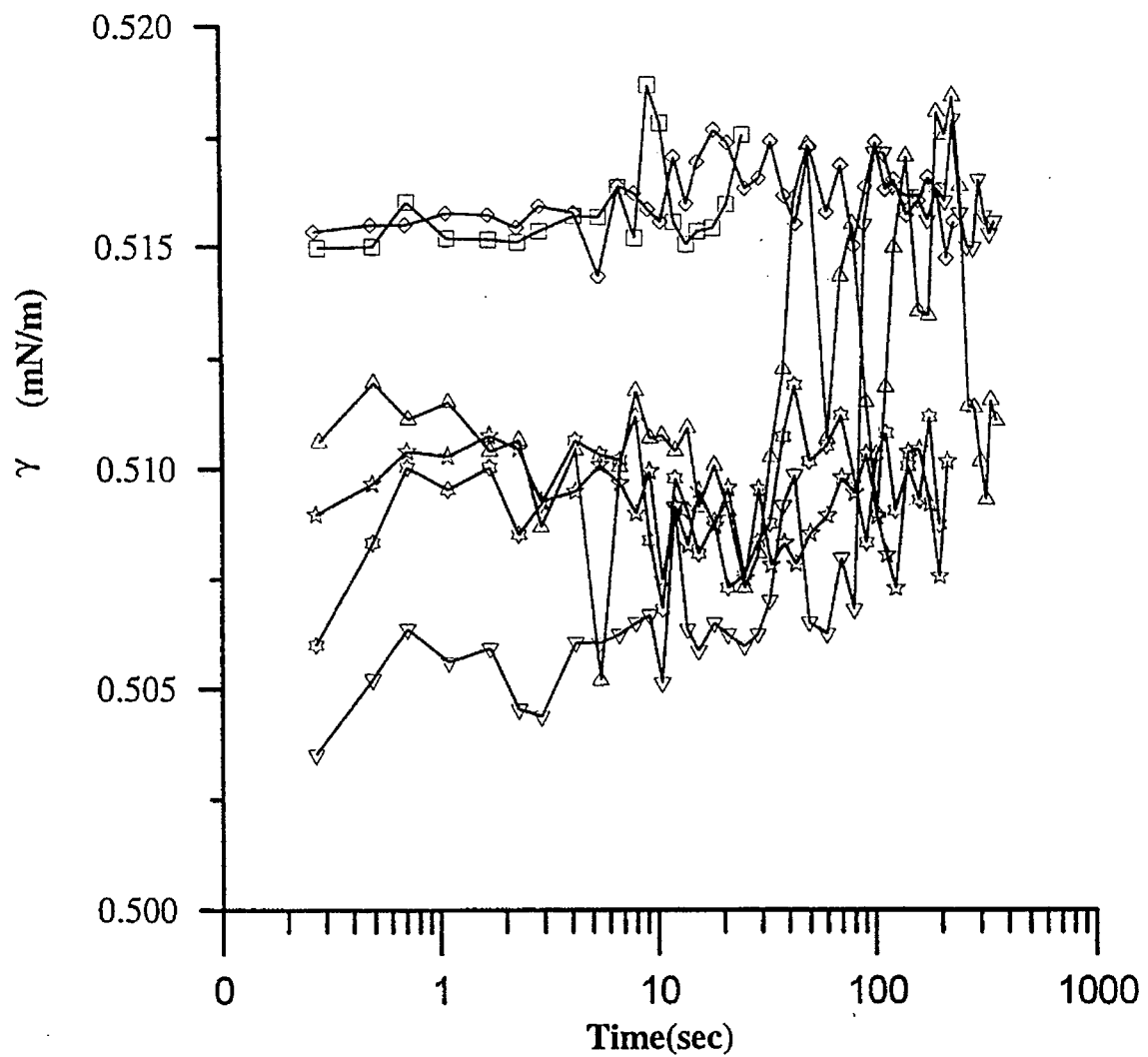

FIGS. 7a–7c show representative dynamic IFT profiles for the water+n-tetradecane+$C_6E_2$ three-coexisting-liquid-phase ternary system measured by the present method at 11.00°±0.02° C. Each different symbol represents a separate drop. Shown in FIG. 7a is the IFT ($\gamma_{\beta\omega}$) of a liquid drop of β (surfactant-rich phase) in ω liquid phase (water-rich phase), the average value is 0.0025±4% mN/m. FIGS. 7b and 7c indicate $\gamma_{\alpha\beta}$=0.516±1.4% mN/m and $\gamma_{\alpha\omega}$=0.511±0.8% mN/m. Values of IFT of this ternary system at several different temperatures are summarized in Table 3 alongside with the values found by using the spinning drop method. The results from the present pendant drop method compare well with the data from the spinning drop method.

2) taking a video image of said silhouette and digitizing said video image such that the loci of a plurality of points at the boundary of said silhouette are obtained;

3) calculating a theoretical curve of the boundary of said silhouette which comprises the following steps:
   a) setting values of $X_0$, $Z_0$, $R_0$ and B, wherein $X_0$ and $Z_0$ are the loci of the apex of said silhouette in the horizontal and vertical directions respectively, $R_0$ is the radius of curvature at the apex, and B is the capillary constant and is defined by $$B = \Delta \rho g R_0^2 / \gamma$$

wherein Δρ is the density difference between the fluid phases, g is the gravitational acceleration constant, and γ is the interfacial tension; and
   b) integrating the following equations:

$$\frac{d\phi}{ds'} = 2 + Bz' - \frac{\sin\phi}{x'}$$

$$\frac{dx'}{ds'} = \cos\phi$$

$$\frac{dz'}{ds'} = \sin\phi$$

with the boundary conditions: x'(0)=z'(0)=s(0)=0, wherein x'=x/$R_0$, z'=z/$R_0$, s'=s/$R_0$; x and z are the loci in the horizontal and vertical directions, s is the arc length measured from the apex, and ψ is the turning angle measured from a horizontal axis;

4) calculating the normal distances between said theoretical curve of step 3) and said a plurality of points at the boundary of said silhouette; and 5) repeating steps 3) and 4) until the sum of the squares of said normal distances is less than a desired value, and computing the interfacial tension wherein $\gamma = \Delta\rho R_0^2 / B$ by using the $R_0$ and B values set in step 3);

wherein the initial $R_0$ and B values are set by the following steps:
   I) selecting two points $P_2$ and $P_1$ from said a plurality of points in step 2), wherein the loci of the $P_2$ and $P_1$ are $(X_1, Z_1)$ and $(X_2, Z_2)$ respectively, and $X_1/Z_1 = A_1$, $X_2/Z_2 = A_2$, $A_1 > A_2$; and
   II) calculating $R_0$ and B values in accordance with the following equations:

TABLE 3

| | Spinning Drop | | | Pendant Drop | | |
|---|---|---|---|---|---|---|
| Temp. (°C.) | $\gamma_{\alpha\beta}$ (mN/m) | $\gamma_{\beta\Omega}$ (mN/m) | $\gamma_{\alpha\Omega}$ (mN/m) | $\gamma_{\alpha\beta}$ (mN/m) | $\gamma_{\beta\Omega}$ (mN/m) | $\gamma_{\alpha\Omega}$ (mN/m) |
| 11.00 ± 0.02 | 0.528 | — | — | 0.516 ± 1.4% | 0.0025 ± 4% | 0.511 ± 0.8% |
| 13.00 ± 0.02 | 0.484 | 0.011 | 0.415 | 0.504 ± 1.6% | 0.021 ± 2% | 0.481 ± 0.2% |
| 17.00 ± 0.02 | 0.439 | 0.064 | 0.375 | 0.400 ± 2.3% | 0.072 ± 1.4% | 0.401 ± 0.2% |

What is claimed is:

1. A method of measuring interfacial tension of a two-phase fluid system by pendant drop digitization comprising the following steps:
   1) forming a pendant drop of a second phase fluid in a first phase fluid and creating a silhouette of said pendant drop;

$$y = a_0 + a_1 w + a_2 w^2 + a_3 w^3 + a_4 w^4 + a_5 w^5$$

$$y' = b_0 + b_1 w + b_2 w^2 + b_3 w^3$$

wherein y=B; y'=$X_2/R_0^2$; w=$X_1/X_2$; $a_0$, $a_1$, $a_2$, $a_3$, $a_4$ and $a_5$ are constants; and $b_0$, $b_1$, $b_2$ and $b_3$ are constants.

* * * * *

UNITED STATES PATENT AND TRADEMARK OFFICE
CERTIFICATE OF CORRECTION

PATENT NO. : 5,615,276
DATED : March 25, 1997
INVENTOR(S) : Lin, et al.

It is certified that error appears in the above-indentified patent and that said Letters Patent is hereby corrected as shown below:

Col. 3, line 24, "$\gamma\left(\frac{1}{R1} + \frac{1}{R2}\right)$" should be -- $\gamma\left(\frac{1}{R1} + \frac{1}{R2}\right) = \Delta P$ --.

Col. 5, line 4, "$X_{A1}/X_2$" should be -- $X_{A1}/X_{A2}$ --.

Col. 5, line 13, "$y' = X_{A2}/R_0 32\ X_2/R_0^2$" should be -- $y' = X_{A2}/R_0 = X_2/R_0^2$ --.

Col. 5, Table 1, Row 7, under heading "$a_4$", "-45103." should be -- -45103.4 --.

Col. 5, Table 2, Row 3, under heading "$b_0$", "13.37873" should be -- 3.37873 --.

Col. 9, line 14, "62" should be -- $\beta$ --.

Col. 9, Table 3, under heading "Spinning Drop", "$\gamma_{\beta\Omega}, \gamma_{\alpha\Omega}$," should be -- $\gamma_{\beta\omega}, \gamma_{\alpha\omega}$ -- and under heading "Pendant Drop", "$\gamma_{\beta\Omega}, \gamma_{\alpha\Omega}$" should be -- $\gamma_{\beta\omega}\ \gamma_{\alpha\omega}$ --.

Signed and Sealed this

Thirtieth Day of September, 1997

Attest:

BRUCE LEHMAN

*Attesting Officer*     *Commissioner of Patents and Trademarks*